United States Patent
Danes et al.

(10) Patent No.: US 9,638,683 B2
(45) Date of Patent: May 2, 2017

(54) SYSTEMS AND METHODS FOR DETERMINING RECYCLED THERMOPLASTIC CONTENT

(71) Applicant: Cal Poly Corporation, San Luis Obispo, CA (US)

(72) Inventors: Jeffrey E. Danes, San Luis Obispo, CA (US); Keith Vorst, San Luis Obispo, CA (US); Greg Curtzwiler, San Luis Obispo, CA (US)

( * ) Notice: Subject to any disclaimer, the term of this patent is extended or adjusted under 35 U.S.C. 154(b) by 477 days.

(21) Appl. No.: 14/216,241

(22) Filed: Mar. 17, 2014

(65) Prior Publication Data
US 2014/0278142 A1 Sep. 18, 2014

Related U.S. Application Data

(60) Provisional application No. 61/800,289, filed on Mar. 15, 2013.

(51) Int. Cl.
*G01N 33/44* (2006.01)

(52) U.S. Cl.
CPC ................. *G01N 33/442* (2013.01)

(58) Field of Classification Search
CPC .................................. G01N 33/442
See application file for complete search history.

(56) References Cited

U.S. PATENT DOCUMENTS

2011/0068262 A1* 3/2011 Vorst ............ G01B 21/08
250/282

* cited by examiner

*Primary Examiner* — Toan Le
(74) *Attorney, Agent, or Firm* — George B Leavell

(57) ABSTRACT

A system and a method for determining a percentage of recycled polyethylene terephthalate present in a test sample includes selecting a contaminant from a set of known contaminants. At least one predictor analyzes is identified from a group of predictor analyzes as being a statistically independent predictor analyzes of a presence of the selected contaminant. Predicting a percent recycled polyethylene terephthalate, identifying at least one set of best subsets of the statistically independent predictor analyzes of percent recycled polyethylene terephthalate and refining a percent recycled polyethylene terephthalate statistical model to a final predicted percent recycled polyethylene terephthalate model.

11 Claims, 6 Drawing Sheets

200
SYSTEMS AND METHODS FOR DETERMINING RECYCLED THERMOPLASTIC CONTENT

CROSS REFERENCE TO RELATED APPLICATIONS

This application claims priority from U.S. Provisional Patent Application No. 61/800,289 filed on Mar. 15, 2013 and entitled "Systems and Methods for Determining Recycled Thermoplastic Content," which is incorporated herein by reference in its entirety.

BACKGROUND

The present invention relates generally to systems and methods for analyzing plastic materials and more particularly, to systems and methods for determining post consumer (i.e. recycled) content in a thermoplastic sample.

Many goods and services are marketed proclaiming percentages of post consumer (i.e., recycled) content in their products and/or product packaging. Reusing post consumer products and packaging materials are an important method of conserving natural resources, energy and reducing bulk in landfills.

Further, many plastic type materials do not decompose naturally for very many years, if at all. Further still, many such plastic type materials breakdown into toxic materials as part of their decomposition process. As a result, recycling such plastic materials are important steps toward reducing the impact of these materials on our environment.

Manufacturers have begun to make broad marketing claims regarding percentages of post consumer material content in their products and product packaging as consumers are becoming more and more aware of the impacts of plastic-type materials on the environment. Unfortunately, for many of these plastic materials, there is no standard, reliable system, method of determining actual contents of a claimed reused or recycled thermoplastic material in a given thermoplastic sample (e.g., a product or a product packaging). As a result, recent testing has shown many of the manufacturers' marketing claims regarding percentages of post consumer material content are less than accurate and some may be specifically misleading to the consumer.

In view of the foregoing, there is a need for standard, reliable systems and methods of determining actual contents of a claimed reused or recycled thermoplastic material in a given thermoplastic sample.

SUMMARY

Broadly speaking, the present invention fills these needs by providing a system and method for determining a percentage of recycled polyethylene terephthalate in a test sample. It should be appreciated that the present invention can be implemented in numerous ways, including as a process, an apparatus, a system, computer readable media, or a device. Several inventive embodiments of the present invention are described below.

One embodiment provides a method for determining a percentage of recycled polyethylene terephthalate present in a test sample. The method includes selecting a contaminant from a set of known contaminants. At least one predictor analyses is identified from a group of predictor analyses as being a statistically independent predictor analyses of a presence of the selected contaminant. Predicting a percent recycled polyethylene terephthalate, identifying at least one set of best subsets of the statistically independent predictor analyses of percent recycled polyethylene terephthalate and refining a percent recycled polyethylene terephthalate statistical model to a final predicted percent recycled polyethylene terephthalate model.

Identifying the at least one predictor analyses from the group predictor analyses as being the statistically independent predictor analyses of the presence of the selected contaminant can include creating a first set of test samples not including the selected contaminant, creating a second set of test samples, each one of the second set of test samples including a different, known percentage of the selected contaminant and analyzing the first set of test samples and the second set of test samples with each one of the group of predictor analyses to produce corresponding contaminant analyses results.

The method can also include selecting a subset of the contaminant analyses results having a Rao's efficiency score $\lambda$ greater than a selected threshold level and applying a binary logistic regression to the selected subset of contaminant analyses results, wherein each one of the statistically independent predictor analyses of the presence of the selected contaminant have a linear combination independence.

Predicting the percent recycled polyethylene terephthalate can include applying a mixed distribution logit-type model including selecting a multiple recycled polyethylene terephthalate samples, each one of the selected recycled polyethylene terephthalate samples including a different, known percentage of the recycled polyethylene terephthalate. Each of the recycled polyethylene terephthalate samples is analyzed with each one of the statistically independent predictor analyses to produce a multiple recycled polyethylene terephthalate observations. The recycled polyethylene terephthalate observations for each one of the predictor analyses can be placed in a corresponding group of mixed distribution logit-type models.

Identifying the at least one set of best subsets of the statistically independent predictor analyses of percent recycled polyethylene terephthalate can include comparing each of the mixed distribution logit-type models to a selected statistical model and selecting a best subset of the statistically independent predictor analyses, each of the selected best subset having a mixed distribution logit-type model that most closely fits the selected statistical model. The best subset of the statistically independent predictor analyses define the percent recycled polyethylene terephthalate statistical model.

Refining the percent recycled polyethylene terephthalate statistical model to the final predicted percent recycled polyethylene terephthalate model can include resealing the selected best subset so that the smallest mixed distribution logit-type model is resealed to 0.

The method can further include applying the at least one set of best subsets of the statistically independent predictor analyses of percent recycled polyethylene terephthalate to a test sample having an unknown percentage of recycled polyethylene terephthalate to produce a plurality of test sample analyses results and comparing the test sample analyses results to the final predicted percent recycled polyethylene terephthalate model to determine a percentage of recycled polyethylene terephthalate in the test sample.

Another embodiment provides a system for determining a percentage of recycled polyethylene terephthalate present in a test sample. The system includes an analyzing apparatus including a controller. The controller includes logic on a computer readable medium for selecting a contaminant from multiple known contaminants, identifying at least one predictor analyses from multiple predictor analyses as being a statistically independent predictor analyses of a presence of the selected contaminant. A percent recycled polyethylene terephthalate is predicted and at least one set of best subsets of the statistically independent predictor analyses of percent recycled polyethylene terephthalate is identified. A percent recycled polyethylene terephthalate statistical model is refined to a final predicted percent recycled polyethylene terephthalate model.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings.

DETAILED DESCRIPTION

Several exemplary embodiments for systems and methods of determining recycled plastic content in a plastic product will now be described. It will be apparent to those skilled in the art that the present invention may be practiced without some or all of the specific details set forth herein.

Measuring recycled plastic content in a plastic product is not a straight forward task. Contaminants such as oil and mold release agents and many more can be introduced into the plastic product during the production cycle of the plastic product. A non-limited, exemplary list of known, common, contaminants include residual monomer, PVC content, aldehydes, heavy metals, antimony, phthalates and various other thermal stabilizers, nucleating agents, colorants, peroxides and other organic compounds.

By way of example, machine oil and hydraulic fluid may contaminate portions of the production machinery that can transfer the machine oil and hydraulic fluid to the plastic product. In another example, the plastic molding machines may be coated with many different types of mold release agents. The mold release agents can be transferred to the plastic product during the molding process. These contaminants can interfere with the accurate analysis of the recycled plastic content in the plastic product. The known contaminates are identified and then statistically eliminated so as to minimize or even eliminate the effects of the contaminants on the recycled plastic content analysis.

The recycled plastic content analysis can yield results to +/−3% accuracy. If less accuracy is desired/required, then a less intensive analysis can be performed. By way of example, fewer analytical steps may provide +/−10% accuracy and still fewer analytical steps may provide +/−20% accuracy.

Systems and Methods for Determining Recycled Thermoplastic Content Recycled Plastic Content Analysis An improved statistical analysis for predicting post-consumer thermoplastic content (PCR) is presented. Previous work in the identification of properties of recycled polyethylene terephthalate (percent RPET) in extruded sheets is described in U.S. Pat. No. 8,063,374, entitled "Systems and Methods for Determining Recycled Thermoplastic Content," issued on Nov. 22, 2011, to Vorst et al, (the '374 patent as referenced herein) and which is incorporated by reference for all purposes.

Figure 1A:
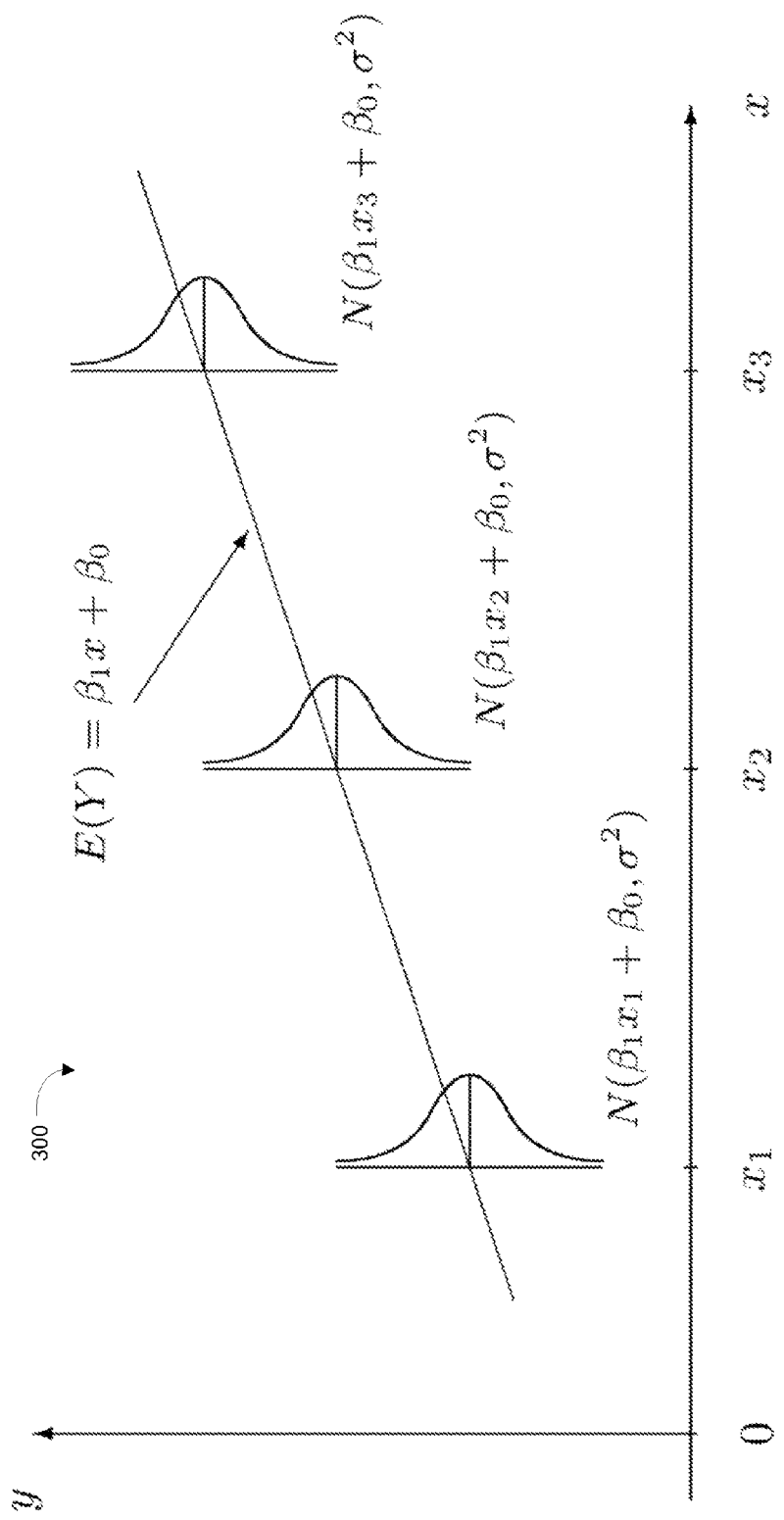
FIG. 1A is a graph of a linear regression, in accordance with embodiments of the present invention.

The '374 patent analyzed PET/RPET sheets using differential scanning calorimetry (DSC), ultraviolet-visible spectroscopy (UV-Vis), electromechanical testing, and inductively coupled plasma-atomic emission spectroscopy (ICP-AES). The resulting data was then examined using linear regression prediction models. FIG. 1A is a graph 100 of a linear regression, in accordance with embodiments of the present invention.

However, the accuracy of the linear regression prediction models of the '374 patent were limited: Predicted percentage of PCR need not be confined to between 0% and 100%. The prediction could be less than 0% or greater than 100%. Further, the errors were not actually occurring in a predicted normal distribution when limiting the PCR analysis to linear regression prediction models. The statistical analyses presented below more accurately model the relationships between percent of RPET and various indicators of percent RPET.

The analysis presented in the '374 patent was performed using sixty (60) polyethylene terephthalate (PET) sheets, each sheet containing between 0% and 100% recycled PET (RPET) of bottle flake. The sixty sheets were produced using typical industrial extruders. The PET/RPET sheets were then analyzed using differential scanning calorimetry, ultraviolet visible spectroscopy, mechanical testing, and inductively coupled plasma-atomic emission spectroscopy (ICP-AES). The light absorbance at 350 nm, percent crystallinity, crystallization temperature and crystallization peak offset were found to be unaffected by the typical silicone mold release coating and were therefore, reasonably valid indicators of percent RPET in the sheet. Table 1 presents all of the analytical tests applied to the test sample sheets.

TABLE 1

Absorption behavior at 350 nm ($A_{350}$ nm)
Crystallization peak onset ($T_c$ onset)
Crystallization temperature ($T_c$)
Crystallization peak offset ($T_c$ offset)
Crystallization peak width ($T_c$ width)
Heat of crystallization ($\Delta H_c$)
Percent % crystallinity
Melting temperature for the first heat cycle ($T_m'$)
Heat of melting for the first heat cycle ($\Delta H_m'$)
Glass transition temperature of the cooling cycle ($T_g$ cool)
Glass transition temperature ($T_g$)
Onset of the melting peak for the second heat cycle ($T_m''$ onset)
Melting temperature of the second heat cycle ($T_m''$)
Offset of the melting peak for the second heat cycle ($T_m''$ offset)
Melting peak width of the second heat cycle ($T_m''$ width); and TABLE 1-continued Heat of melting for the second heat cycle (Δ H$_m$")
DEG Content

---

Mechanical testing has determined that incorporating recycled content into virgin PET resin significantly alters the composite mechanical properties. Specifically, analysis indicated that there was between about 2 and about 30 MPa (megaPascal) increase in stress at the proportional limit, stress at yield, and Young's modulus, respectively, in the machine direction at 40% RPET concentration when compared to a PET sheet of 100% virgin resin.

Figure 1B:
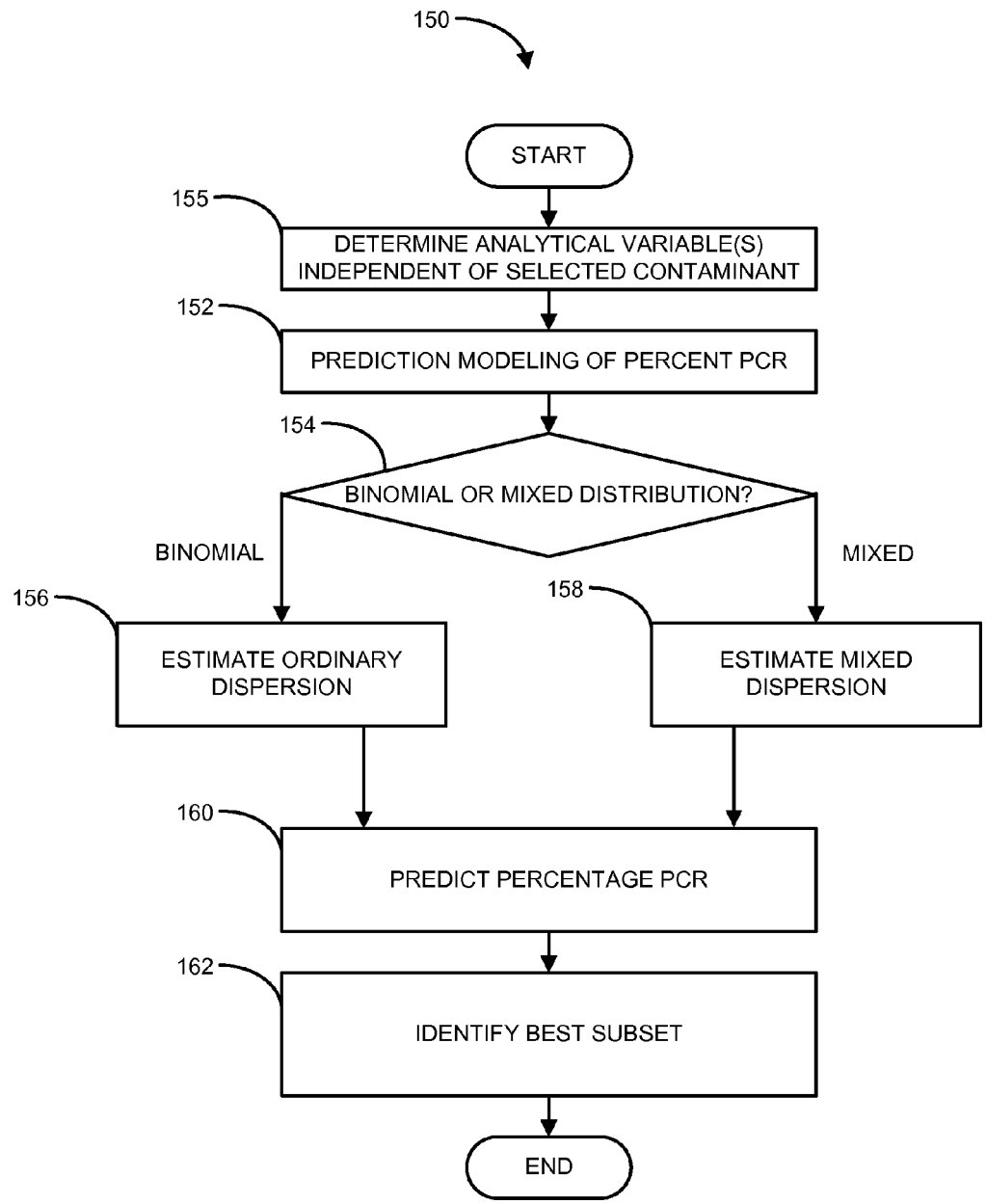
FIG. 1B is a flowchart of the method operations for determining RPET content, in accordance with an embodiment of the present invention.

FIG. 1B is a flowchart of the method operations 150 for determining RPET content, in accordance with an embodiment of the present invention. The method operations 150 for determining RPET content generally includes three main steps: Step 1 screens contaminants, in an operation 152; Step 2 predicts percent RPET, in operations 154-160; and Step 3 identifies the best subsets of predictors of percent RPET, in an operation 162.

Step 1 screens contaminants, and as shown in the example below, identifies contaminant independent analyses for the silicone mold release coating. However it should be understood that other contaminants can also be screened from the analytical data. A binary logistic model, as described in "Theoretical Statistics" (1974) by Cox and Henkley, is used to identify a subset of variables that are independent of the selected contaminant.

In simple terms, the process of identifying contaminant dependent tests includes creating two RPET sample sets of various percentages of PCR, one set with the contaminant and one without the contaminant. Each set is then analyzed using as many as the 17+ test variables shown in Table 1 above and as described in more detail below (mechanical measurements are included here) to predict percent PCR. If there is an overall significant difference in prediction, then the contaminant is not independent from (i.e., IS dependent on) the predictor test. However, if there is no significant difference in predicting percent PCR, then the predictor test is statistically independent of the contaminant.

Step 2 of predicting percent RPET applies a mixed distribution logit-type model as will be described in more detail below. Step 3 identifies the best subsets of predictors of percent RPET. Best subsets are identified using Akiake's adjusted Information Criterion, "AICc" as described in "Likelihood of a Model and Information Criteria," (1981) by H. Akaike, as published in the Journal of Economics, 16, 3-14.

Step 1: Determination of Independent Subsets

The first task is to identify a subset of predictor variables that are independent of the contaminant, the silicone coating. For example, the silicone mold release is scored 1=coating and 0=no coating and is used as the dependent variable in a binary logistic model. To accomplish this objective, Rao's 1973 published works is used to obtain an efficient score. For example, the 17 analyses listed in Table 1 above and data summarized in Table 2: Means, SD, and Influence of the "contaminant" (mold release) as follows:

TABLE 2

| Variable | Mean | SD | λ-Score | Probability |
|---|---|---|---|---|
| Hc | 24.49 | 1.40 | 12.754 | <0.001 |
| Tg | 83.26 | 2.18 | 12.467 | <0.001 |
| Hm" | 30.77 | 3.38 | 11.756 | <0.001 |

TABLE 2-continued

| Variable | Mean | SD | λ-Score | Probability |
|---|---|---|---|---|
| Tc width | 13.00 | 2.07 | 7.815 | 0.005 |
| Tm" offset | 254.38 | 1.16 | 6.687 | 0.010 |
| DEG Content | 4.09 | 0.21 | 4.902 | 0.027 |
| Tm" | 248.50 | 1.18 | 4.902 | 0.027 |
| Tg Reverse | 74.82 | 1.65 | 3.544 | 0.060 |
| Hm' | 34.83 | 2.13 | 2.879 | 0.090 |
| Tc offset | 144.16 | 3.48 | 1.318 | 0.251 |
| Tc onset | 131.16 | 1.91 | 0.895 | 0.344 |
| Tm" onset | 227.89 | 3.05 | 0.707 | 0.400 |
| Crystal | 8.99 | 1.71 | 0.496 | 0.481 |
| Tm' | 251.67 | 1.38 | 0.108 | 0.742 |
| Tc | 137.55 | 2.06 | 0.032 | 0.859 |
| Tm" idth | 26.49 | 2.50 | 0.030 | 0.863 |
| A350nm | 1.56 | 0.15 | 0.003 | 0.958 |

Rao's efficient score, λ, measures an initial contribution a variable makes in predicting an outcome. Rao's efficient score, λ is commonly used as an initial screening tool in forward selection analyses. In typical forward selection analyses, if a potential predictor has a sufficiently significant λ-score, such as exceeding a selected level or setpoint, (e.g., a selected level of Rao's efficient score, λ) the predictor is selected for further analysis. It should be noted that Rao's efficient score, λ, is only one example of a statistical analytical tool to evaluate the data. Other suitable statistical analytical tools can also be used.

However, in example application, the goal was to identify analyses that are independent of the selected contaminant, the silicone mold release in this instance, thus non-significant linear combinations of indicators were sought. In line with this objective, the eight variables reported in Table 2 with λ-scores with p>0.10 were identified as potentially independent of the contaminant factor of the mold release because they exceed a selected p-score setpoint or level, in this instance 0.10.

To identify the linear combination of variables, independent of the silicone mold release, the systematic "directed search" selection method described in "Fitting Equations to Data", (1980) Second Edition, by C. Daniel and F. S. Woods. Variables with the smallest λ-scores (high p values) were entered into a binary logistic regression one at a time. After each entry, a $\chi^2$ test for linear dependence and the Cox-Snell $R^2$ was calculated, as described in "analysis of Binary Data" (1989), Second Edition by D. R. Cox and E. J. Snell. This process obtains a statistically significant linear combination. The results are presented in Table 3.

TABLE 3

| Variable Added | $X^2$ | df | Probability | $R^2$ |
|---|---|---|---|---|
| A350nm | 0.003 | 1 | 0.958 | 0.000 |
| Tm"width | 0.042 | 2 | 0.979 | 0.001 |
| Tc | 0.274 | 3 | 0.965 | 0.005 |
| Tm' | 0.719 | 4 | 0.949 | 0.012 |
| Crystal | 3.186 | 5 | 0.671 | 0.052 |
| Tm"Onset | 18.859 | 6 | 0.004 | 0.270 |

The systematic test of nested variables reveals the five analyses results that are statistically independent predictor analyses of the mold release contaminant factor: A350 nm, Tm" width, Tc, Tm', and % Crystal. The linear combination independence requirement breaks down when the sixth variable, Tm" onset, is entered in the binary logistic regression, $\chi^2$=18.86, df=6, p=0.004, and the Cox-Snell $R^2$=0.27, see Table 3. It should be noted that the mold release contamination is merely one example of a contaminant that can be selected to find the statistically independent predictor analyses that are independent of the selected contaminant.

Figure 4:
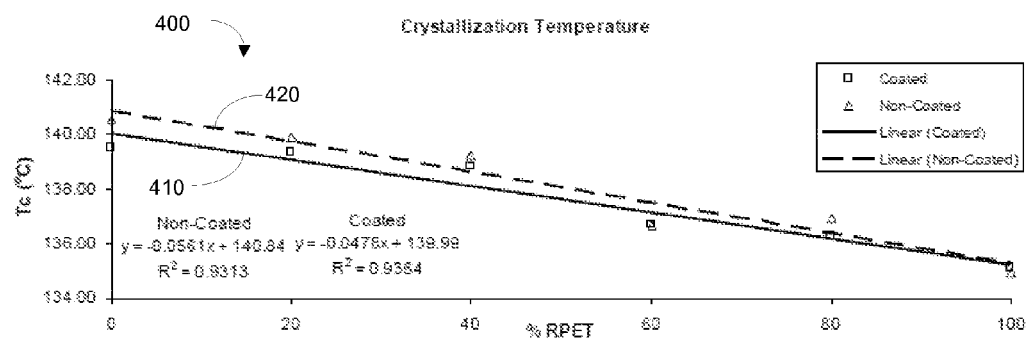
FIG. 4 is an exemplary regression graph of crystallization temperature (Tc), in accordance embodiments of the present invention.

FIG. 4 is an exemplary regression graph 400 of crystallization temperature (Tc), in accordance embodiments of the present invention. Graph 410 represents the linear regression of the crystallization temperature (Tc) of the RPET samples not coated with the mold release compound expressed as: Tc(non-coated)=−0.0561(% RPET)+140.84 degrees C. Graph 420 represents the linear regression of the crystallization temperature (Tc) of the RPET samples coated with the mold release compound expressed as:

Tc(coated)=−0.0478(% RPET)+139.99 degrees C.

Step 2: Mixed Distribution Logit Model

A generalized logit model is in the family of link-function linear models developed by Nelder and Wedderburn, in their 1972 published works, and further refined as described in "Generalized Linear Models," (1989), Second Edition, by Peter McCullagh and John Nelder. For the present data set ($Y_i$, $X_i$, $w_i$) the following definitions apply, i=1, . . . , n denotes the 60 observations, is a binomial count corresponding to percent RPET, $X_i$ is the vector of the predictor variables (Table 3), and $w_i$ is the prior weight for criterion $Y_i$. The goal of the analysis is to identify the "best" subset of percent RPET predictors. For this purpose the generalized logit model for extra-binomial variation is employed.

Table 4 presents exemplary link functions and mean functions to enable custom modeling.

TABLE 4

| Distribution | Link Function | Mean Function |
| --- | --- | --- |
| Normal | $X\beta = \eta$ | $\eta = X\beta$ |
| Exponential | $X\beta = \eta^{-1}$ | $\eta = (X\beta)^{-1}$ |
| Gamma | | |
| Poisson | $X\beta = \ln(\eta)$ | $\eta = \exp(X\beta)$ |
| Binomial | $X\beta = \ln(\pi/1-\pi)$ | $\pi = \dfrac{\exp(X\beta)}{1 + \exp(X\beta)}$ |
| Multinomial | | |

Figure 5:
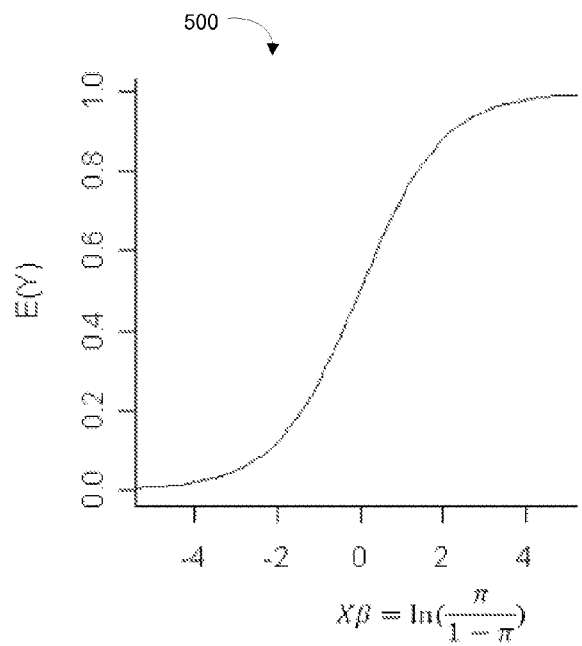
FIG. 5 is a graph of an exemplary mixed distribution model, in accordance embodiments of the present invention.

FIG. 5 is a graph 500 of an exemplary mixed distribution model, in accordance embodiments of the present invention. This example experiment has six equal levels of $Y_i$ (percent RPET): 0, 20, 40, 60, 80, 100% and is uniformly distributed. Thus the data set represents a mixed distribution. The number of observations are denoted, i=1, 2, . . . , n. $Y_i$ is the implied binomial count of the number of "successes" out of $m_i=m=100$ trials. For each of the six selected percentages of RPET there are 10 observations for a total of n=60 observations. Following the model II described "Extra-Binomial Variation in Linear Logit Models," (1982), by D. A. Williams, Applied Statistics 34(2), 144-148, the expected value and variance are given as follows:

$$t(Y_i) = m\pi_i \quad [1]$$

$$Var(Y_i) = \phi w_i^{-1} m\pi_i(1-\pi_i) \quad [2]$$

Where $\phi w_i^{-1}$ represents the extra-binomial variation and $\phi$ is given by $[1+\rho(m-1)]$ where $\rho$ is a parameter that represents the deviation from normal binomial dispersion; $w_i^{-1}$ is a prior weight. A constant $\rho$ is assumed for all proportions.

The generalized logit model is defined by two functions g and r the link function $g(\pi_i)=\eta_i$ is a monotonic differentiable link function relating the mean probability (or binomial proportion)

$$\pi_i = E\left(\frac{y_i}{m}\right)$$

to the linear predictor $\eta=X\beta$ where X is an n×p design matrix, $\beta$ is a p×1 vector of regression coefficients.

Figure 2:
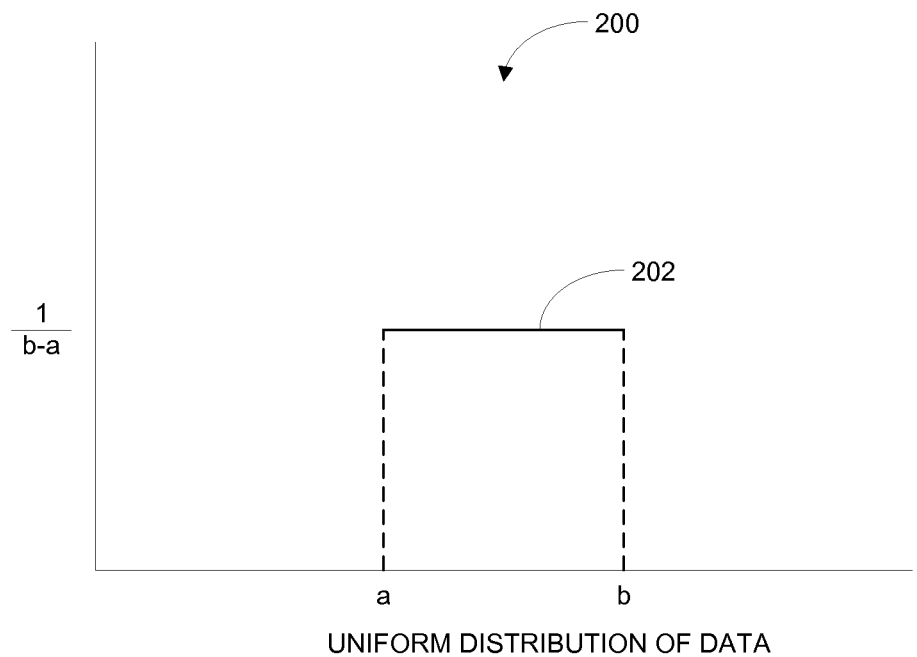
FIG. 2 illustrates a graph of uniform distribution, in accordance with embodiments of the present invention.
Figure 3:
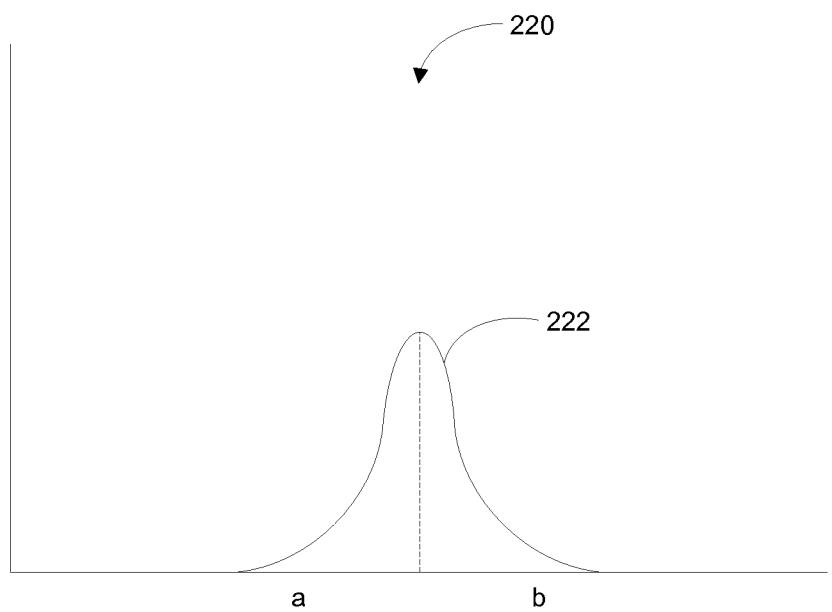
FIG. 3 illustrates a graph of normal distribution, in accordance with embodiments of the present invention.

The variance function v relates the variance with the expected binomial count, $m\pi_i$, to the variance by $Var(Y_i)=\phi w^{-1}v(\pi_i)$ where $\phi=m\phi$. For the binomial distribution $v(\pi_i)=\pi_i(1-\pi_i)$ and the scale factor $\phi=1$ and $w_i=1$ under ideal conditions. However, in this instance the observed values for $Y_i$ are uniformly distributed over six levels: 0, 20, 40 60, 80, and 100. FIG. 2 illustrates a graph 200 of uniform distribution, in accordance with embodiments of the present invention. Note the graph 200 shows all the data points falling in a straight line 202. In contrast, FIG. 3 illustrates a graph 220 of normal distribution, in accordance with embodiments of the present invention. The graph 220 shows the data points falling in a "bell-shaped" curve 222 having a peak substantially centered and the data points gradually decreasing from the peak, toward zero, on either side of the peak.

The five potential predictors identified in Table 3 were studied in the following analysis. The generalized logit model was defined as the following link-linear function:

$$\eta_i = g(\pi_i) = \Sigma_j \beta_j \chi_{ij}, i=1, \ldots, n. \quad [3]$$

With the logit link function g such that:

$$E(Y_i/m) = \pi_i \quad (4)$$
$$= g^{-1}\left(\ln\left[\frac{\pi_i}{1-\pi_i}\right]\right),$$

Where:

$$\sum_j \beta_j x_{ij} = \ln\left(\frac{\pi_i}{1-\pi_i}\right) \quad (5)$$

And where $\pi_i$ is the probability corresponding to the percentage of RPET.

Step 3: Best Subset Predictors of Percentage of RPET

From the five eligible variables reported in Table 3, the next step in the analysis is to identify the "best" subsets Akaike's information criteria was used to evaluate the relative quality of the generalized logit models as described in Akaike 1973 published works and in "Further Analysis of the Data by Akaike's Information Criterion and the Finite Correction," (1978), by N. Sugiura Communication in Statistics, A7, 713-26 and in "Model Selection and Multi-Model Inference, a Practical Information-Theoretic Approach," (2002) by K. P. Burnham and D. R. Anderson, second edition. The five variables give 26 subset models. Each subset model was evaluated using the finite sample corrected Akaike Information Criterion, AICc.

$$AICc = -2*(L) + \frac{2k(n+m)}{(n+m)-k-1}, \quad [6]$$

Where L is the log likelihood function, k=p+1 is the number of predictors plus the intercept in the model, n is the number of observations and m is the number of trials. Table 5 presents the Akaike corrected information criterion for all possible subset models:

TABLE 5

| | Deviance | Scale | X² | ΔAICc |
|---|---|---|---|---|
| df = 54 | | | | |
| A350nm, Tm"width, Tc, Tm', Crystal | 49.2 | 0.9 | 40.6 | 3.2 |
| df = 55 | | | | |
| A350nm, Tm"width, Tc, Tm' | 49.3 | 0.9 | 40.7 | 1.3 |
| A350nm, Tm"width, Tc, Crystal | 52.0 | 0.9 | 42.6 | 4.0 |
| A350nm, Tm"width, Tm', Crystal | 49.8 | 0.9 | 41.2 | 1.8 |
| A350nm, Tc, Tm', Crystal | 55.0 | 1.0 | 43.7 | 7.0 |
| Tm"width, Tc, Tm', Crystal | 99.3 | 1.8 | 89.1 | 51.3 |
| df = 56 | | | | |
| A350nm, Tm"width, Tc | 52.3 | 0.9 | 43.0 | 2.4 |
| A350nm, Tm"width, Tm' | 50.0 | 0.9 | 41.3 | 0.0 |
| A350nm, Tm"width, Crystal | 52.6 | 0.9 | 43.2 | 2.6 |
| A350nm, Tc, Tm' | 56.2 | 1.0 | 44.4 | 6.2 |
| A350nm, Tc, Crystal | 55.8 | 1.0 | 44.7 | 5.8 |
| A350nm, Tm', Crystal | 56.9 | 1.0 | 45.2 | 6.9 |
| Tm"width, Tc, Tm' | 138.6 | 2.5 | 118.2 | 88.6 |
| Tm"width, Tc, Crystal | 106.0 | 1.9 | 91.7 | 56.0 |
| Tm" width, Tm', Crystal | 158.6 | 2.8 | 145.7 | 108.6 |
| Tc, Tm', Crystal | 113.7 | 2.0 | 99.4 | 63.7 |
| df = 57 | | | | |
| A350nm, Tm" width | 53.1 | 0.9 | 43.7 | 1.1 |
| A350nm, Tc | 57.0 | 1.0 | 45.5 | 5.0 |
| A350nm, Tm' | 58.8 | 1.0 | 46.3 | 6.8 |
| A350nm, Crystal | 57.6 | 1.0 | 46.0 | 5.6 |
| Tm" width, Tc | 156.7 | 2.7 | 130.5 | 104.7 |
| Tm" width, Tm' | 408.4 | 7.2 | 335.5 | 356.4 |
| Tm" width, Crystal | 170.6 | 3.0 | 153.7 | 118.7 |
| Tc, Tm' | 209.3 | 3.7 | 169.7 | 157.3 |
| Tc, Crystal | 116.2 | 2.0 | 100.3 | 64.3 |
| Tm', Crystal | 160.5 | 2.8 | 145.8 | 108.5 |
| df = 58 | | | | |
| A350nm | 59.5 | 1.0 | 47.3 | 5.5 |
| Tm" width | 561.5 | 9.7 | 444.7 | 507.5 |
| Tc | 218.6 | 3.8 | 174.9 | 164.6 |
| Tm' | 515.2 | 8.9 | 409.6 | 461.2 |
| Crystal | 170.7 | 2.9 | 153.9 | 116.7 |

In Table 5, model fit is given as Δfit (relative fit), relative to the minimum value, so that the smallest AICc is resealed to 0. Out of the 26 possible models, the best model is the three variable model with predictors: A350 nm, Tm" width, and Tm', as shown in the following Table 6:

TABLE 6

| Parameter | B | df | SE(model)* | Prob. | SE(robust) | Prob. |
|---|---|---|---|---|---|---|
| (Intercept) | −45.75 | 1 | 17.067 | 0.007 | 17.496 | 0.009 |
| Tm"width | 0.16 | 1 | 0.272 | 0.001 | 0.247 | <0.001 |
| A350nm | 4.78 | 1 | 0.048 | <0.001 | 0.044 | <0.001 |
| Tm' | 0.14 | 1 | 0.067 | 0.043 | 0.068 | 0.040 |

*standard errors are scale adjusted

Table 7 presents the predicted percentage of RPC values:

TABLE 7

| | Actual: | | | | | |
|---|---|---|---|---|---|---|
| | 0% | 20% | 40% | 60% | 80% | 100% |
| Mean % | 2.72 | 19.45 | 31.54 | 71.22 | 79.48 | 95.59 |
| SD | 1.28 | 2.27 | 7.92 | 5.97 | 4.35 | 1.40 |
| SE mean | 0.40 | 0.72 | 2.50 | 1.89 | 1.38 | 0.44 |
| Percentile 25 | 2.13 | 18.03 | 25.35 | 66.51 | 76.07 | 94.38 |
| Median | 2.34 | 19.10 | 30.91 | 70.37 | 79.79 | 95.38 |
| Percentile 75 | 2.81 | 20.71 | 34.93 | 75.5 | 83.10 | 96.94 |
| Min | 1.50 | 15.26 | 21.49 | 64.85 | 73.15 | 93.45 |
| Max | 5.97 | 22.70 | 47.23 | 82.31 | 86.42 | 97.58 |
| N | 10 | 10 | 10 | 10 | 10 | 10 |

Table 8 presents the absolute and standard deviation errors in the predicted percentage of RPC values:

TABLE 8

| | | Actual: | | | | | |
|---|---|---|---|---|---|---|---|
| | | 0% | 20% | 40% | 60% | 80% | 100% |
| Prediction | MEAN | 2.7 | 19.5 | 31.5 | 71.2 | 79.5 | 95.6 |
| Abs (error) | | 4.6 | 2.7 | 0.6 | 8.5 | 11.2 | 0.5 | 4.4 |
| SD (error) | | 3.9 | 1.3 | 2.3 | 7.9 | 6.0 | 4.4 | 1.4 |

Figure 6:
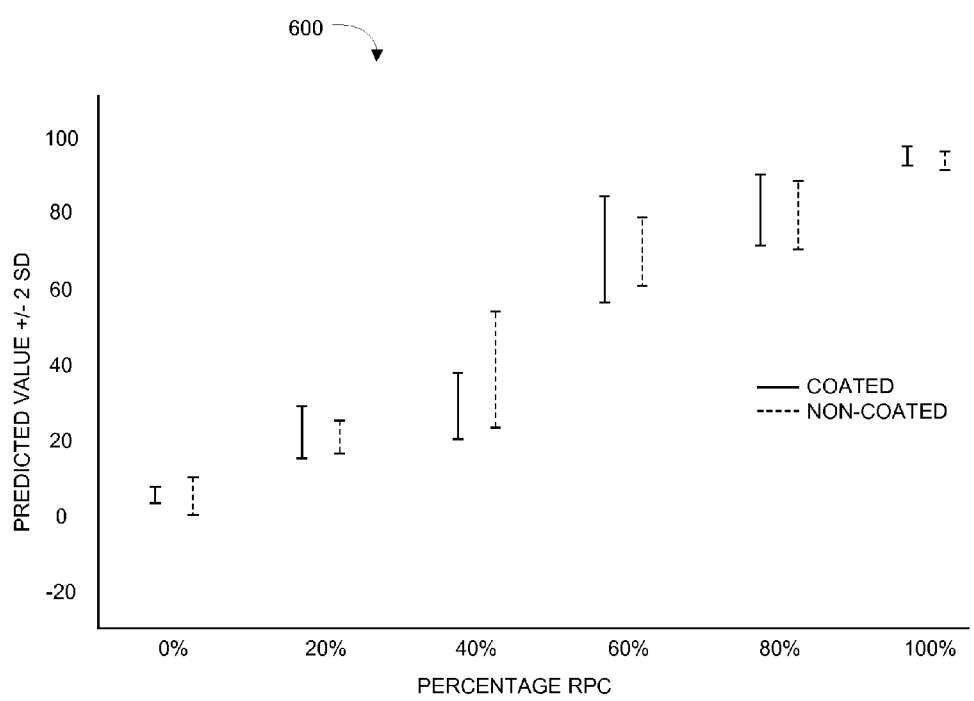
FIG. 6 is a graph of the predicted percentage RPC values +/− two standard deviations as shown in Table 7, in accordance with embodiments of the present invention.

FIG. 6 is a graph 600 of the predicted percentage RPC values +/− two standard deviations as shown in Table 7, in accordance with embodiments of the present invention.

The invention can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, DVDs, Flash, magnetic tapes, and other optical and non-optical data storage devices. The computer readable medium can also be distributed over a network coupled computer systems so that the computer readable code is stored and executed in a distributed fashion.

Any of the operations described herein that form part of the invention are useful machine operations. The invention also relates to a device or an apparatus for performing these operations. The apparatus may be specially constructed for the required purposes, or it may be a general-purpose computer selectively activated or configured by a computer program stored in the computer. In particular, various general-purpose machines may be used with computer programs written in accordance with the teachings herein, or it may be more convenient to construct a more specialized apparatus to perform the required operations.

Figure 7:
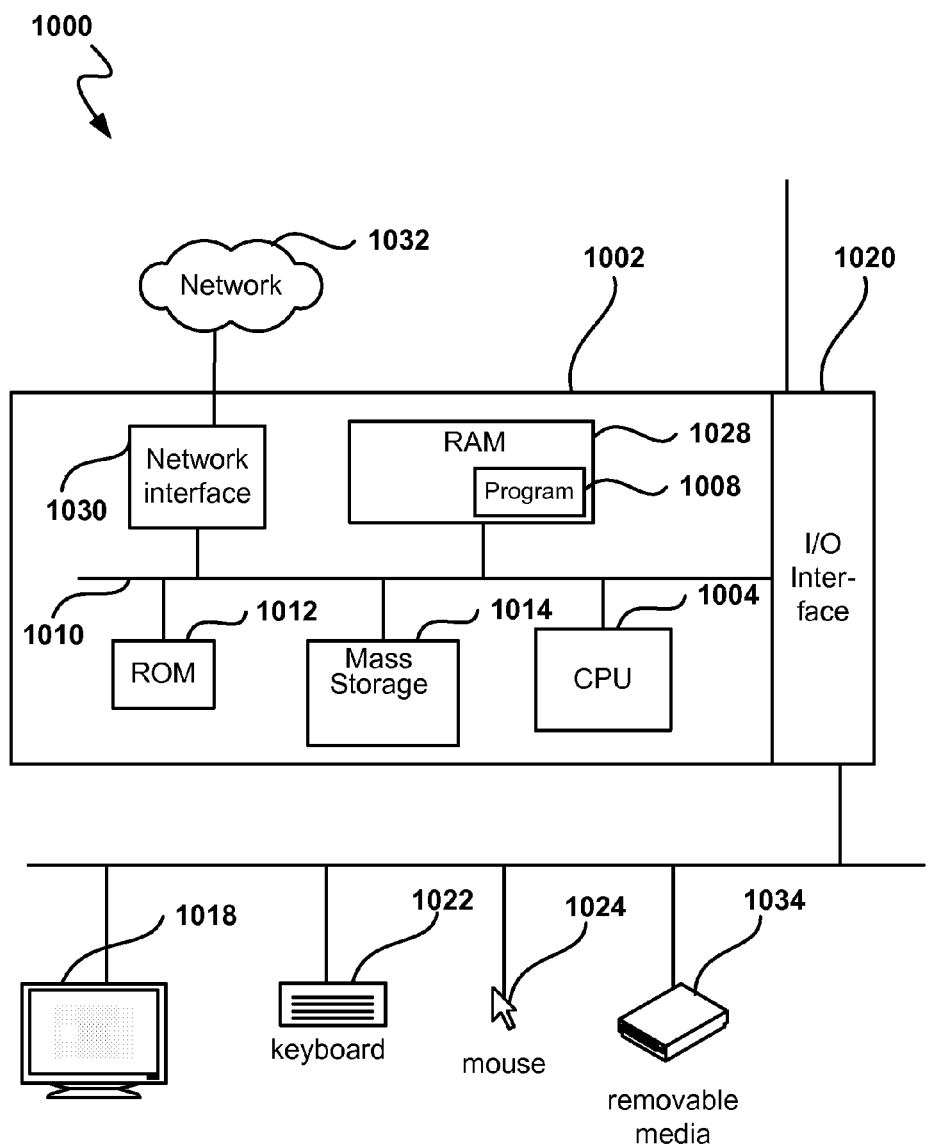
FIG. 7 is a block diagram of an example computer system for carrying out the processing according to the invention.

FIG. 7 is a block diagram of an example computer system 1000 for carrying out the processing according to the invention. A general or specialized computer system, such as the computer system 1000, can be used as a controller for controlling a system executing the operations for performing at least a portion of the analyses described above. The computer system 1000 includes a computer 1002, a display 1018, an optional printer or output device (not shown), a removable media (e.g., magnetic/optical/flash) drive 1034, a mass storage system 1014 (e.g., hard disk drive, solid state drive, or other suitable data storage device), a network interface 1030, and a keyboard 1022. Additional user interface devices such as a mouse 1024, a touch pad or touch screen can also be included.

The computer 1002 includes a central processing unit 1004, one or more data buses 1010, random access memory (RAM) 1028, read only memory (ROM) 1012, and an input/output interface 1020. The computer 1002 can be a personal computer (such as an IBM compatible personal computer, a Macintosh computer or Macintosh compatible computer), a workstation computer (such as a Sun Microsystems or Hewlett-Packard workstation), or some other suitable type of computer.

The CPU 1004 can be a general purpose digital processor or a specially designed processor. The CPU 1004 controls the operation of the computer system 1000. Using instructions retrieved from memory (e.g. program(s) 1008), the CPU 1004 controls the reception and manipulation of input data and the output and display of data on output devices.

The data buses 1010 are used by the CPU 1004 to access the RAM 1028, the ROM 1012 and the mass storage 1014. The RAM 1028 is used by the CPU 1004 as a general storage area and as scratch-pad memory, and can also be used to store input data and processed data. The RAM 1028 and the ROM 1012 can be used to store computer readable instructions or program code 1008 readable and executable by the CPU 1004 as well as other data.

The bus 1010 can also be used to access the input, output, and storage devices used by the computer 1002. These devices include the display 1018, the optional printer (not shown), the removable media drive 1034, and the network interface 1030. The input/output interface 1020 is used to receive input from keyboard 1022 and send decoded symbols for each pressed key to CPU 1004 over the data bus 1010.

The display 1018 is an output device that displays images of data provided by the CPU 1004 via the bus 1010 or provided by other components in the computer system 1000. The optional printer device, when operating as a printer, provides an image on a sheet of paper or a similar surface. Other output devices such as a plotter, projector, etc. can be used in place of, or in addition to, the printer device.

The removable media drive 1034 and the mass storage 1014 can be used to store various types of data. The removable media drive 1034 facilitates transporting such data to other computer systems, and mass storage 1014 permits fast access to large amounts of stored data. The mass storage 1014 may be included within the computer system or may be external to the computer system such as network attached storage or cloud storage accessible over one or more networks (e.g., local area networks, wide area networks, wireless networks, Internet 1032) or combinations of such storage devices and locations.

The CPU 1004 together with an operating system operate to execute computer readable code and logic and produce and use data. The computer code, logic and data may reside within the RAM 1028, the ROM 1012, or the mass storage 1014 or other media storage devices and combinations thereof. The computer code and data could also reside on a removable program medium and loaded or installed onto the computer system 1000 when needed. Removable program media include, for example, DVD, CD-ROM, PC-CARD, floppy disk, flash memory, optical media and magnetic disk or tape.

The network interface 1030 is used to send and receive data over a network 1032 connected to other computer systems. An interface card or similar device and appropriate software implemented by the CPU 1004 can be used to connect the computer system 1000 to an existing network and transfer data according to standard protocols such as local area networks, wide area networks, wireless networks, Internet and any other suitable networks and network protocols.

The keyboard 1022 is used by a user to input commands and other instructions to the computer system 1000. Other types of user input devices can also be used in conjunction with the present invention. For example, pointing devices such as a computer mouse, a track ball, a stylus, touch pad, touch screen or a tablet can be used to manipulate a pointer on a screen of a general-purpose computer.

It will be further appreciated that the instructions represented by the operations in the above figures are not required to be performed in the order illustrated, and that all the processing represented by the operations may not be necessary to practice the invention. It should also be appreciated that some operations may have sub-operations and in other instances, certain operations described herein may not be included in the illustrated operations. Further, the processes described in any of the above figures can also be implemented in software stored in any one of or combinations of the RAM, the ROM, or the hard disk drive.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A method for determining a percentage of recycled polyethylene terephthalate present in a test sample using a computer comprising:

receiving in the computer, a selection of a contaminant from a plurality of contaminants;

identifying by the computer at least one predictor analyses from a plurality of predictor analyses as being a statistically independent predictor analyses of a presence of the selected contaminant using a binary logit model in non-transitory computer readable media, wherein the binary logit model includes test sample analytical data received from at least one of a plurality of analytical systems for analyzing the test sample and producing the test sample analytical data;

performing a prediction of a percent recycled polyethylene terephthalate statistical model by the computer, based on the at least one predictor analyses, performing the prediction including determining a probability corresponding to the percent recycled polyethylene terephthalate using a logic link function in non-transitory computer readable media;

performing an identification by the computer of at least one set of best subsets of the statistically independent predictor analyses of percent recycled polyethylene terephthalate, using a finite sample corrected Akaike Information Criterion function in non-transitory computer readable media to produce a plurality of subset models;

performing a refinement by the computer of the percent recycled polyethylene terephthalate statistical model to a final predicted percent recycled polyethylene terephthalate model, including comparing each of the plurality of subset models to identify one of the plurality of subset models having minimum value relative fit using a refinement function in non-transitory computer readable media and rescaling the selected best subset so that the smallest mixed distribution logit-type model is rescaled to 0; and identifying and outputting the percent recycled polyethylene in a test sample using the final predicted percent recycled polyethylene terephthalate model, wherein the plurality of analytical systems for analyzing the test sample include at least one of a mechanical stress tester, a differential scanning calorimeter, an ultraviolet visible spectroscope and an inductively coupled plasma-atomic emission spectroscope.

2. The method of claim 1, wherein identifying the at least one predictor analyses from the plurality of predictor analyses as being the statistically independent predictor analyses of the presence of the selected contaminant includes:
providing a first set of test samples not including the selected contaminant;
providing a second set of test samples, each one of the second set of test samples including a different, known percentage of the selected contaminant; and
performing an analysis by the computer of the first set of test samples and the second set of test samples using a contaminant analysis function in non-transitory computer readable media including using the plurality of predictor analyses to produce a plurality of contaminant analyses results.

3. The method of claim 2, further comprising:
performing a selection by the computer of a subset of the plurality of contaminant analyses results having a Rao's efficiency score λ greater than a selected threshold level; and
applying by the computer a binary logistic regression to the selected subset of contaminant analyses results, wherein the binary logistic regression is included in non-transitory computer readable media, wherein each one of the statistically independent predictor analyses of the presence of the selected contaminant have a linear combination independence.

4. The method of claim 3, wherein performing the prediction of the percent recycled polyethylene terephthalate includes applying a mixed distribution logit-type model by the computer including:
receiving a selection by the computer of a plurality of recycled polyethylene terephthalate samples, each one of the selected recycled polyethylene terephthalate samples including a different, known percentage of the recycled polyethylene terephthalate;
performing an analysis by the computer of each of the plurality of recycled polyethylene terephthalate samples with each one of the statistically independent predictor analyses to produce a plurality of recycled polyethylene terephthalate observations; and
placing by the computer the plurality of recycled polyethylene terephthalate observations for each one of the plurality of predictor analyses in a corresponding plurality of mixed distribution logit-type models.

5. The method of claim 1, further comprising:
applying by the computer at least one set of best subsets of the statistically independent predictor analyses of percent recycled polyethylene terephthalate to a test sample having an unknown percentage of recycled polyethylene terephthalate to produce a plurality of test sample analyses results; and
performing a comparison by the computer of the plurality of test sample analyses results to the final predicted percent recycled polyethylene terephthalate model.

6. A method for determining a percentage of recycled polyethylene terephthalate present in a test sample using a computer comprising:
receiving in the computer, a selection of a contaminant from a plurality of contaminants;
identifying by the computer at least one predictor analyses from a plurality of predictor analyses as being a statistically independent predictor analyses of a presence of the selected contaminant using a binary logit model in non-transitory computer readable media, wherein the binary logit model includes test sample analytical data received from at least one of a plurality of analytical systems for analyzing the test sample and producing the test sample analytical data;
performing a prediction of a percent recycled polyethylene terephthalate statistical model by the computer, based on the at least one predictor analyses, performing the prediction including determining a probability corresponding to the percent recycled polyethylene terephthalate using a logic link function in non-transitory computer readable media including:
receiving a selection by the computer of a plurality of recycled polyethylene terephthalate samples, each one of the selected recycled polyethylene terephthalate samples including a different, known percentage of the recycled polyethylene terephthalate;
performing an analysis by the computer of each of the plurality of recycled polyethylene terephthalate samples with each one of a statistically independent predictor analyses to produce a plurality of recycled polyethylene terephthalate observations; and
placing by the computer the plurality of recycled polyethylene terephthalate observations for each one of the plurality of predictor analyses in a corresponding plurality of mixed distribution logit-type models;
performing an identification by the computer of at least one set of best subsets of the statistically independent predictor analyses of percent recycled polyethylene terephthalate, using a finite sample corrected Akaike Information Criterion function in non-transitory computer readable media to produce a plurality of subset models;
performing a refinement by the computer of the percent recycled polyethylene terephthalate statistical model to a final predicted percent recycled polyethylene terephthalate model, including comparing each of the plurality of subset models to identify one of the plurality of subset models having minimum value relative fit using a refinement function in non-transitory computer readable media;
applying by the computer the at least one set of best subsets of the plurality of predictor analyses of percent recycled polyethylene terephthalate to a test sample having an unknown percentage of recycled polyethylene terephthalate to produce a plurality of test sample analyses results;
comparing by the computer the plurality of test sample analyses results to the final predicted percent recycled polyethylene terephthalate model and rescaling the selected best subset so that the smallest mixed distribution logit-type model is rescaled to 0; and
identifying and outputting the percent recycled polyethylene in a test sample using the final predicted percent recycled polyethylene terephthalate model, wherein the plurality of analytical systems for analyzing the test sample include at least one of a mechanical stress tester, a differential scanning calorimeter, an ultraviolet visible spectroscope and an inductively coupled plasma-atomic emission spectroscope.

7. A system for determining a percentage of recycled polyethylene terephthalate present in a test sample using a computer comprising:
an analyzing apparatus including a controller, the controller including:

logic on a non-transitory computer readable medium for receiving in the computer, a selection of a contaminant from a plurality of contaminants;

logic on a non-transitory computer readable medium for identifying by the computer at least one predictor analyses from a plurality of predictor analyses as being a statistically independent predictor analyses of a presence of the selected contaminant using a binary logit model in non-transitory computer readable media, wherein the binary logit model includes test sample analytical data received from at least one of a plurality of analytical systems for analyzing the test sample and producing the test sample analytical data;

logic on a non-transitory computer readable medium for performing a prediction of a percent recycled polyethylene terephthalate statistical model by the computer, based on the at least one predictor analyses, performing the prediction including determining a probability corresponding to the percent recycled polyethylene terephthalate using a logic link function in non-transitory computer readable media;

logic on a non-transitory computer readable medium for performing an identification by the computer of at least one set of best subsets of the statistically independent predictor analyses of percent recycled polyethylene terephthalate, using a finite sample corrected Akaike Information Criterion function in non-transitory computer readable media to produce a plurality of subset models;

logic on a non-transitory computer readable medium for performing a refinement by the computer of the percent recycled polyethylene terephthalate statistical model to a final predicted percent recycled polyethylene terephthalate model, including comparing each of the plurality of subset models to identify one of the plurality of subset models having minimum value relative fit using a refinement function in non-transitory computer readable media and rescaling the selected best subset so that the smallest mixed distribution logit-type model is rescaled to 0; and logic on a non-transitory computer readable medium for identifying and outputting the percent recycled polyethylene in a test sample using the final predicted percent recycled polyethylene terephthalate model, wherein the plurality of analytical systems for analyzing the test sample include at least one of a mechanical stress tester, a differential scanning calorimeter, an ultraviolet visible spectroscope and an inductively coupled plasma-atomic emission spectroscope.

8. The system of claim 7, wherein the logic on the on-transitory computer readable medium for identifying by the computer the at least one predictor analyses from the plurality of predictor analyses as being the statistically independent predictor analyses of the presence of the selected contaminant using the binary logit model in non-transitory computer readable media includes:

logic on a non-transitory computer readable medium for providing a first set of test samples not including the selected contaminant;

logic on a non-transitory computer readable medium for providing a second set of test samples, each one of the second set of test samples including a different, known percentage of the selected contaminant; and logic on a non-transitory computer readable medium for performing an analysis by the computer of the first set of test samples and the second set of test samples using a contaminant analysis function in non-transitory computer readable media including using the plurality of predictor analyses to produce a plurality of contaminant analyses results.

9. The system of claim 8, further comprising:

logic on a non-transitory computer readable medium for performing a selection by the computer of a subset of the plurality of contaminant analyses results having a Rao's efficiency score $\lambda$ greater than a selected threshold level; and logic on a non-transitory computer readable medium for applying by the computer a binary logistic regression to the selected subset of contaminant analyses results, wherein the binary logistic regression is included in non-transitory computer readable media, wherein each one of the statistically independent predictor analyses of the presence of the selected contaminant have a linear combination independence.

10. The system of claim 7, wherein the logic the non-transitory computer readable medium for wherein performing the prediction of the percent recycled polyethylene terephthalate includes applying a mixed distribution logit-type model by the computer including:

logic on a non-transitory computer readable medium for receiving a selection by the computer of a plurality of recycled polyethylene terephthalate samples, each one of the selected recycled polyethylene terephthalate samples including a different, known percentage of the recycled polyethylene terephthalate;

logic on a non-transitory computer readable medium for performing an analysis by the computer of each of the plurality of recycled polyethylene terephthalate samples with each one of the statistically independent predictor analyses to produce a plurality of recycled polyethylene terephthalate observations; and logic on a non-transitory computer readable medium for placing by the computer the plurality of recycled polyethylene terephthalate observations for each one of the plurality of predictor analyses in a corresponding plurality of mixed distribution logit-type models.

11. The system of claim 7, further comprising:

logic on a non-transitory computer readable medium for applying by the computer at least one set of best subsets of the plurality of predictor analyses of percent recycled polyethylene terephthalate to a test sample having an unknown percentage of recycled polyethylene terephthalate to produce a plurality of test sample analyses results; and logic on a non-transitory computer readable medium for performing a comparison by the computer of the plurality of test sample analyses results to the final predicted percent recycled polyethylene terephthalate model.

* * * * *